United States Patent [19]
Kobayashi et al.

[11] 3,993,696
[45] Nov. 23, 1976

[54] METHOD FOR RECOVERING HYDROPEROXIDE

[75] Inventors: Katsumi Kobayashi, Minoo; Iwao Dohgane, Ashiya; Yukimichi Nakao, Kobe, all of Japan

[73] Assignee: Sumitomo Chemical Company, Limited, Osaka, Japan

[22] Filed: Apr. 29, 1974

[21] Appl. No.: 465,137

[30] Foreign Application Priority Data
May 2, 1973 Japan.............................. 48-49407

[52] U.S. Cl. .................. 260/610 A; 260/610 B; 203/92; 203/91; 203/95; 203/97
[51] Int. Cl.² ................................. C07C 179/02
[58] Field of Search ........ 260/610 A, 610 B, 621 A; 203/91, 92, 93, 95, 96, 97

[56] References Cited
UNITED STATES PATENTS

| | | | |
|---|---|---|---|
| 2,632,026 | 3/1953 | Conner | 260/610 A |
| 2,706,708 | 4/1955 | Frank et al. | 202/46 |
| 2,715,646 | 8/1955 | Hawkins | 260/610 A |
| 2,856,433 | 10/1958 | Thompson | 260/610 A |
| 2,915,558 | 12/1959 | Alder | 260/610 A |
| 3,883,600 | 5/1975 | Miller | 260/610 A |

FOREIGN PATENTS OR APPLICATIONS

| | | | |
|---|---|---|---|
| 920,013 | 3/1963 | Germany | 260/610 A |
| 641,250 | 8/1950 | United Kingdom | 260/610 B |

*Primary Examiner*—James O. Thomas, Jr.
*Assistant Examiner*—W. B. Lone
*Attorney, Agent, or Firm*—Stevens, Davis, Miller & Mosher

[57] ABSTRACT

Diisopropylbenzene monohydroperoxide which is usable for the oxidation of diisopropylbenzene without prevention of the oxidation, is recovered from an oxidation product solution of diisopropylbenzene by steam-distilling the oxidation product solution at pH 6 to 9 and at a solution temperature of 80° to 130° C under a reduced pressure.

7 Claims, No Drawings

METHOD FOR RECOVERING HYDROPEROXIDE

The present invention relates to a method for recovering diisopropylbenzene monohydroperoxide of the formula,

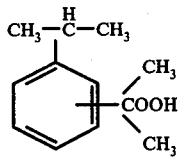

(referred to as M-HPO for brevity), from an oxidation product solution of diisopropylbenzene of the formula,

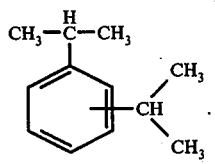

It is known that the diisopropylbenzene is oxidized with molecular oxygen to afford an oxidation product solution containing unreacted diisopropylbenzene, M-HPO and diisopropylbenzene dihydroperoxide of the formula,

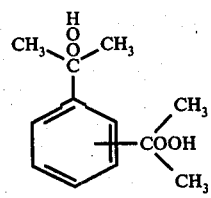

(referred to as D-HPO for brevity), and then the resulting oxidation product solution is subjected to extraction with an aqueous alkaline solution, whereby the solution is separated into an oily layer containing M-HPO and an aqueous layer containing D-HPO. It is also known that p-diisopropylbenzene is oxidized to afford an oxidation product solution, which is successively followed by cooling to obtain para-D-HPO as crystals. Further, it is well known that the said oily layer containing M-HPO, which is considered to be a precursor of D-HPO, can be recycled to the said oxidation. The reuse of the oily layer containing M-HPO as such for the oxidation reaction of the diisopropylbenzene, however, will prevent the oxidation reaction from proceeding, because the oxidation product solution contains, aside from unoxidized diisopropylbenzene, M-HPO and D-HPO, a large number of by-products have carbinol group, carbonyl group, carboxyl group or the like, which will be accumulated in the reaction system, unless they can be removed out of the system together with D-HPO in the separation of D-HPO. According to the aforesaid conventional separation procedures, such as the separation of D-HPO using an aqueous alkaline solution and the separation thereof by crystallization, however, all byproducts other than by-products having carboxyl group remain in the oily layer together with M-HPO, so that the oily layer as such cannot be reused without prevention of the oxidation reaction. Accordingly, it is important from industrial point of view to recover M-HPO capable of reusing for the oxidation reaction.

On the other hand, it has been reported in British Pat. No. 641,250 that M-HPO has a vapor pressure as low as $2.5 \times 10^{-2}$ mmHg at 84° C, that is, the oxidation product is subjected to distillation in order to clarify the composition of the oxidation product, and then M-HPO is obtained under $2.5 \times 10^{-2}$ mmHg at 80° to 90° C.

The present inventors have studied to find a method for the recovery of M-HPO from the oxidation product solution of diisopropylbenzene, which method can be easily carried out in an industrial scale without using disadvantageously severe conditions, and found that M-HPO, which can be reused for the oxidation of diisopropylbenzene without any disadvantage can be recovered by steam-distillation of the oxidation product solution freed from D-HPO according to the conventional method, under a certain condition.

Thus, the present invention provides a method for recovering M-HPO from the oxidation product solution, which comprises separating D-HPO from the oxidation product solution according to the conventional method, and conducting a steam-distillation of the resulting oxidation product solution at pH 6 to 9 and at a solution temperature of 80° to 130° C under a reduced pressure.

In other words, in a method for producing diisopropylbenzene dihydroperoxide by (1) oxidizing diisopropylbenzene with molecular oxygen to obtain an oxidation product solution containing unoxidized diisopropylbenzene, diisopropylbenzene monohydroperoxide, diisopropylbenzene dihydroperoxide and oxidation byproducts, (2) separating diisopropylbenzene dihydroperoxide from the oxidation product solution, and (3) recycling the oxidation product solution freed from diisopropylbenzene dihydroperoxide to the oxidation step (1), the present invention provides an improvement which comprises adjusting the said oxidation product solution freed from diisopropylbenzene dihydroperoxide to pH 6 to 9, steam-distilling the resulting oxidation product solution at a solution temperature of 80° to 130° C under a reduced pressure, cooling the distillate to be separated into an oily layer containing unoxidized diisopropylbenzene and diisopropylbenzene monohydroperoxide, and an aqueous layer, and recycling the oily layer to the oxidation step (1).

The method of the present invention will be explained in more detail as follows.

The oxidation product solution obtained by oxidizing the diisopropylbenzene, for example, using molecular oxygen, is treated to separate D-HPO contained in the solution by the conventional method, such as extraction of D-HPO with an aqueous alkaline solution, and crystallization thereof, which methods are described in British Pat. Nos. 641,250 and 739,907, and the resulting oxidation product solution freed from D-HPO is adjusted to pH 6 to 9, preferably pH about 7, and subjected to the steam-distillation under a reduced pressure. The adjusting of the pH can be conducted, preferably by washing the oxidation product solution with water, or by using an acid such as acetic acid and sulfuric acid, or an alkali such as sodium carbonate and sodium hydroxide. The reduced pressure is from 20 to 300 mmHg, preferably from 50 to 150 mmHg. The solution temperature of the steam-distillation is from 80° to 130° C, preferably from 100° to 110° C. The amount of steam to be introduced varies depending upon the distillation temperature, degree of reduced pressure, composition of the oxidation product solution to be steam-distilled and type of a reactor (distillator), but it is usually within a range from about 3 to about 10 times by weight the oxidation product solution freed from D-HPO. Thus, M-HPO can be distilled out together with steam, and the distillate is cooled through a condenser to separate into an oily layer containing M-HPO and unoxidized diisopropylbenzene, and an aqueous layer. The oily layer can be recycled to the oxidation reaction of diisopropylbenzene to obtain D-HPO without any disadvantages.

Although M-HPO can be distilled out by steam-distillation of the oxidation product solution containing D-HPO, it is favorable to separate D-HPO prior to the steam-distillation because a thermal decomposition of D-HPO occurs under the conditions mentioned above. As is clear from Experiments 1 to 5 in the following Table 1, it is unfavorable in consideration of the retention of M-HPO to conduct the steam-distillation beyond the limits of pH mentioned above. Accordingly, the oxidation product solution to be subjected to the steam-distillation is favorably neutralized in advance, for example, by washing with water. As for the solution temperature during the steam-distillation, the steam-distillation at below 80° C leads to decrease of a distillation amount of M-HPO, resulting in unfavorable distillation efficiency. On the other hand, the steam-distillation at higher than 130° C leads to thermal decomposition of M-HPO to decrease the retention percent thereof, and moreover it is dangerous because the possibility of sudden thermal-decomposition is increased. According to the same reason, it is favorable to lower the temperature of the distillate as low as possible. The temperature of the distillate can be lowered with increasing the degree of reduced pressure, but it becomes difficult more and more to condense the distillate by cooling. Therefore, in carrying out the present steam-distillation in an industrial scale, the temperature of the distillate will be determined depending upon the degree of reduced pressure in consideration of several factors concerning a distillation apparatus.

Even if the steam-distillation is conducted within the above-defined range of the solution temperature, the object of the present invention cannot be accomplished when the steam-distillation is conducted under an atmospheric pressure, as is clear from Experiment No. 14 in the following Table I. Accordingly, it is essential condition to conduct the steam-distillation at the solution temperature of 80° to 130° C and under a reduced pressure. In order to keep the solution temperature favorably to 100° to 110° C even after the introduction of steam under a reduced pressure, heating will be required. An external heating can be applied. Alternatively, a method which comprises supplying a preheated oxidation product solution which is freed from D-HPO, can be applied, particularly for continuously carrying out the method of the present invention. The distillate can easily be separated into the oily layer containing M-HPO and unoxidized diisopropylbenzene, and the aqueous layer after the condensation by cooling. The solubility of M-HPO in the aqueous layer is so negligible that substantially no M-HPO is lost into the aqueous layer.

Table I

| Experiment No. | pH of oxidation product solution | Solution temperature (° C) | Degree of reduced pressure (mmHg) | Recovery percent of M-HPO (%) | Retention percent of M-HPO (%) |
|---|---|---|---|---|---|
| 1 | 5 | 105 | 100 | 64 | 71 |
| 2 | 6 | 105 | 100 | 86 | 92 |
| 3 | 7 | 105 | 100 | 88 | 98 |
| 4 | 9 | 105 | 100 | 86 | 90 |
| 5 | 11 | 105 | 100 | 11 | 29 |
| 6 | 7 | 70 | 100 | 24 | 100 |
| 7 | 7 | 75 | 100 | 33 | 100 |
| 8 | 7 | 80 | 100 | 58 | 99 |
| 9 | 7 | 90 | 100 | 73 | 99 |
| 10 | 7 | 100 | 100 | 86 | 98 |
| 11 | 7 | 110 | 100 | 85 | 94 |
| 12 | 7 | 120 | 100 | 63 | 74 |
| 13 | 7 | 130 | 100 | 48 | 51 |
| 14 | 7 | 105 | Atmospheric pressure | 4 | 87 |
| 15 | 7 | 105 | 300 | 60 | 88 |
| 16 | 7 | 105 | 50 | 91 | 89 |

Note:
The oxidation product solution used in the Experiments was prepared by oxidizing diisopropylbenzene (0 : m : p = 0.2 : 62.0 : 37.8) according to the conventional method, and separation D-HPO from the resulting oxidation product solution by the conventional method.

Control of pH was conducted using acetic acid, diluted sulfuric acid, sodium hydroxide and sodium carbonate, or by washing with water.

In order to clarify the relationship between the solution temperature and the degree of reduced pressure, the amount of steam in each Experiment was made as constant as possible with attention, and was within a range between 5 and 6 times by weight the oxidation product solution.

The recovery percentage of M-HPO $$= \frac{\text{(M-HPO contained in the oily layer as the distillate)}}{\begin{pmatrix}\text{M-HPO contained in the oxidation product solution}\\ \text{before the steam-distillation}\end{pmatrix}} \times 100$$

The retention percentage of M-HPO $$= \frac{\begin{pmatrix}\text{M-HPO contained in the distillate and the}\\ \text{solution remaining in the distillator}\end{pmatrix}}{\begin{pmatrix}\text{M-HPO contained in the oxidation product}\\ \text{solution before the steam-distillation}\end{pmatrix}} \times 100$$

The present invention will be explained in more detail with reference to the following Example, which is only illustrative, but not limitative for the scope of the present invention. In Example, parts are by weight unless otherwise specified.

EXAMPLE

100 Parts of an oxidation product solution of diisopropylbenzene freed from D-HPO [45 parts of diisopropylbenzene (o : m : p = 0.1 : 58.4 : 41.5), 45 parts of M-HPO and 10 parts of byproducts having carbinol group mainly] was washed with water to adjust the pH to 7, and was placed in a 200 parts by volume heart type flask equipped with a thermometer, a steam inlet pipe and a condenser. The content was heated on an oil bath of 125° to 130° C, and steam of 1 atm. by gauge was introduced thereinto for 2 hours at a rate of 280 parts per hour. The procedure was controlled to make the degree of reduced pressure 100 mmHg and the solution temperature 105° to 110° C. The distillate temperature was 85° to 95° C.

From the distillate the aqueous layer was separated to obtain 85 parts of an oily layer. The oily layer contained 45 parts of the diisopropylbenzene and 40 parts of M-HPO. On the other hand, the distillation residue was 15 parts, and contained 4 parts of M-HPO and 11 parts of total byproducts having carbinol group. From the results, the recovery percentage of M-HPO was calculated as 88 % and the retention percentage of M-HPO 98 %.

The resulting oily layer containing diisopropylbenzene and M-HPO was recycled to the oxidation reaction system, and the oxidation reaction could be carried out efficiently without any disadvantage.

What is claimed is:

1. In a method for recovering diisopropylbenzene monohydroperoxide from an oxidation product solution containing unoxidized diisopropylbenzene, diisopropylbenzene monohydroperoxide, diisopropylbenzene dihydroperoxide and oxidation byproducts, which oxidation product solution is prepared by the oxidation of diisopropylbenzene, and successively by the separation of diisopropylbenzene dihydroperoxide from the resulting oxidation product, the improvement which comprises introducing steam into the oxidation product solution at pH 6 to 9 and at a solution temperature of 80° to 130° C under a reduced pressure to obtain a distillate consisting of an aqueous layer and an oil layer comprising diisopropylbenzene monohydroperoxide, and separating the distillate into the aqueous layer and the oil layer.

2. The method according to claim 1, wherein the reduced pressure is from 20 to 300 mmHg.

3. The method according to claim 1, wherein the steam-distilling is conducted under external heating.

4. The method according to claim 1, wherein the steam-distilling is conducted by feeding the pre-heated oxidation product solution freed from diisopropylbenzene dihydroperoxide.

5. The method according to claim 1, wherein the method is conducted batchwise or continuously.

6. In a method for producing diisopropylbenzene dihydroperoxide by (1) oxidizing diisopropylbenzene with molecular oxygen to obtain an oxidation product solution containing unoxidized diisopropylbenzene, diisopropylbenzene monohydroperoxide, diisopropylbenzene dihydroperoxide and oxidation byproducts, (2) separating diisopropylbenzene dihydroperoxide from the oxidation product solution, and (3) recycling the oxidation product solution freed from diisopropylbenzene dihydroperoxide to the oxidation step (1), an improvement which comprises introducing steam into the oxidation product solution at pH 6 to 9, at a solution temperature of 80° C to 130° C under a reduced pressure of from 20 to 300 mmHg to obtain a distillate, cooling the distillate consisting of an oily layer containing unoxidized diisopropylbenzene and diisopropylbenzene monohydroperoxide, and an aqueous layer, separating the distillate into the aqueous layer and the oil layer, and recycling the oily layer to the oxidation step (1).

7. The improvement according to claim 6, wherein the pH of the oxidation product solution is adjusted by washing the oxidation product solution with water, or by using acetic acid, sulfuric acid, hydrochloric acid, sodium carbonate or sodium hydroxide.

* * * * *